United States Patent [19]
Hrdlicka et al.

[11] Patent Number: 6,038,480
[45] Date of Patent: Mar. 14, 2000

[54] LIVING TISSUE STIMULATION AND RECORDING TECHNIQUES WITH LOCAL CONTROL OF ACTIVE SITES

[75] Inventors: Gregory A. Hrdlicka, Plymouth; Gary W. King, Fridley, both of Minn.

[73] Assignee: Medtronic, Inc., Minneapolis, Minn.

[21] Appl. No.: 09/024,162

[22] Filed: Feb. 17, 1998

Related U.S. Application Data

[63] Continuation-in-part of application No. 08/627,576, Apr. 4, 1996, abandoned.

[51] Int. Cl.$^7$ ..................................................... A61N 1/05
[52] U.S. Cl. ......................... 607/116; 600/393; 600/373; 607/2
[58] Field of Search ...................... 607/116, 122, 607/129, 117, 118, 148, 119, 46, 2; 600/393, 377, 374, 373, 378

[56] References Cited

U.S. PATENT DOCUMENTS

| | | | |
|---|---|---|---|
| 3,920,024 | 11/1975 | Bowers | 128/419 PG |
| 3,957,036 | 5/1976 | Normann | 128/2.1 R |
| 4,524,774 | 6/1985 | Hildebrandt | 128/421 |
| 4,543,955 | 10/1985 | Schroeppel | 128/635 |
| 4,570,640 | 2/1986 | Barsa | 128/741 |
| 4,702,254 | 10/1987 | Zabara | 128/421 |
| 4,750,499 | 6/1988 | Hoffer | 128/784 |
| 4,867,164 | 9/1989 | Zabara | 128/421 |
| 4,877,032 | 10/1989 | Heinze et al. | 607/9 |
| 4,964,411 | 10/1990 | Johnson et al. | 128/733 |
| 5,018,523 | 5/1991 | Bach, Jr. et al. | 128/419 PG |
| 5,025,807 | 6/1991 | Zabara | 128/421 |
| 5,081,990 | 1/1992 | Deletis | 128/642 |
| 5,167,229 | 12/1992 | Peckham et al. | 128/421 |
| 5,314,458 | 5/1994 | Najafi et al. | 607/116 |
| 5,314,495 | 5/1994 | Kovacs | 607/48 |

(List continued on next page.)

FOREIGN PATENT DOCUMENTS

| | | | |
|---|---|---|---|
| 0236513 | 9/1987 | European Pat. Off. | A61B 5/04 |
| 9519804 | 7/1995 | WIPO | A61N 1/05 |

OTHER PUBLICATIONS

Jay D. Law, Spinal Stimulations: Statistical Superiority of Monophasic Stimulation Nowly Separated, Longitudianl Bipoles Having Rostral Cthodes, *Proc. of Amer. Soc. Sterotatctic and Functional Neurosurgry, Appl. Neurophysiol* 46, pp. 129–137 (1983).

Holsheimer et al., "Contract Combinations in Epidural Spinal Cord Stimulation," *Sterotact Funct Neurosurg*, 56, pp. 220–233 (1991).

Holsheimer et al., "How Do Geometric Factors Influence Epidural Spinal Cord Stimulation," *Stereotact Funct Neurosurg*, 56, pp. 234–249(1991).

North et al., "Spinal Cord Stimulation for Chronic, Intractabel Pain: Superiority of Multi–Channel Devices," *Pain*, 44, pp. 119–130(1991).

Barolat et al., "Mapping of Sensory Responses to Epidural Stimulation for the Intraspinal Neural Structures in Man", *I Neurosurg.* 78, pp. 233–239 (1993).

Struijk, et al., "Paaresthesia Thresholds in Spinal Cord Stimulation: A Comparision of Theotetical Results with Clinical Dates", *IEEE Transactions on Rehabiliation Engineering*, vol. 1, No. 2, (Jun. 1993).

(List continued on next page.)

*Primary Examiner*—Kennedy J. Schaetzle
*Attorney, Agent, or Firm*—Banner & Witcoff, Ltd.

[57] ABSTRACT

Implantable electrodes adapted to interact with electrically excitable tissue are selected by an implantable, programmable controller that receives power from a main cable and data from a data conductor that identifies the stimulation and recording electrodes to be activated. The implantable controller enables electrical signals to be transmitted between a distal site of power generation and a selected subset of multiple electrodes with a minimum number of conductor wires.

31 Claims, 7 Drawing Sheets

U.S. PATENT DOCUMENTS

| | | | |
|---|---|---|---|
| 5,325,870 | 7/1994 | Kroll et al. | 607/122 |
| 5,411,547 | 5/1995 | Causey, III | 607/129 |
| 5,417,719 | 5/1995 | Hull et al. | 607/46 |
| 5,423,873 | 6/1995 | Neubauer et al. | 607/68 |
| 5,531,774 | 7/1996 | Schulman et al. | 607/56 |
| 5,593,430 | 1/1997 | Renger | 607/18 |

OTHER PUBLICATIONS

Struijk and Holsheimer, "Transvere tripolar spinal cord stimulatin: theoretical performance of dual channel system", *Medical & Biological Engineering & Computing*, pp. 273–279 (Jul. 1996).

Barolat et al., "Mulifactorial Analysis of Epidural Spinal Cord Stimulation", *Stereotact Funct Neurosurg*, 56, pp. 77–103 (1991).

Agnew et al., "Effect of prolonged electrical stimulation fo the central nervous stystem," *Neural Prostheses: Fundamental Studies,* Chapter 9, Prentice–Hall, Englewood Cliffs(1990).

Center for Integrated Sensors and Circuits, "Thin–Film Intracortical Recording Microelectrodes", Neural Prosheses Program Quarterly Report No. 11 (Apr.–Jun. 1996).

Center for Integrated Sensors and Circuits, "Thin–Film Intracortical Recording Microelectrodes", Neural Prosthese Program Quarterly Report No. 7 (Apr.–Jun. 1995).

Center for Integrated Sensors and Circuits, "Micromachined Stimulating Electrodes", Neural Prosheses Program, Quarterly Report No. 4 (Jul.–Sep. 1996).

Heinrich Bantli, Ph.D., et al., "Supraspinal Interatios Resulting form Experimetnal Dorsal Column Stimulation," Journal of Neurosurgery, vol. 42, Mar., 1975, pp. 296–300.

LIVING TISSUE STIMULATION AND RECORDING TECHNIQUES WITH LOCAL CONTROL OF ACTIVE SITES

This is a continuation-in-part of the earlier filed patent application Ser. No. 08/627,576 filed on Apr. 4, 1996, now abandoned, for which priority is claimed. This parent application is incorporated herewith by reference.

BACKGROUND OF THE INVENTION

1. Field of the Invention

This invention relates to an implantable system for stimulating electrically excitable tissue within a patient and recording potentials of such tissue in the patient, and more particularly relates to such a system in which the stimulating and recording electrodes are selectable to reduce the number of conductors to a minimum.

2. Description of the Related Art

Often it is desirable with spinal cord or deep brain stimulation for pain relief or control of movement disorders to have many stimulation electrodes on a stimulation lead in order to place one or more cathodes and one or more anodes in optimal locations to produce benefits or minimize undesirable side effects. Implanted systems now use one to three leads and have between one and sixteen stimulation electrodes. Such systems typically must pass up to 20 milliamperes of current or more, involving current densities of 10 microcoulombs per square centimeter per phase or more. As a result, each electrode is connected to a sizable conductor in order to minimize energy losses due to impedance and to provide adequate strength to connect the wire to a power supply without substantial risk of breakage. Most current systems have the ability to program the polarity of each electrode. Due to size limitations and properties of conductors, it is difficult to have high reliability when there are eight, sixteen or more wires within a lead body that is implanted in a patient.

A lead with twenty to fifty or more stimulation electrodes could be useful for some therapies. Optimal combinations of cathodes and anodes could be selected for each patient. However, the use of this many electrodes has not been feasible in the past because of the size limitations imposed by the need to have a sizable conductor connected to each electrode. The present invention is directed to solving this problem.

A tripole lead is shown in PCT Publication No. WO95/19804 (Jul. 27, 1995). However, such a lead lacks the ability to reprogram electrodes, and clinical benefit is critically dependent on electrode positioning. This invention overcomes the disadvantages of the foregoing lead by allowing changes in an effective stimulation area after implant by programming.

SUMMARY OF THE INVENTION

The invention is useful for interacting with electrically excitable tissue of a patient. According to the preferred embodiment, a group of implantable electrodes is adapted to interact with the tissue. A main cable extends from a first site to a second site adjacent the tissue. A source of data identifies one or more of the electrodes within the group, and a data conductor extends from the source of data to the second site. An implantable controller is responsive to the data for gating one or more of the electrodes to the main cable.

The invention enables electrical signals to be transmitted between the first site and one or more selectable electrodes within the patient with a minimum number of conductors. As a result, the number of electrodes implanted in the patient can be substantially increased in order to provide improved therapeutic effects. By minimizing the number of conductors, reliability is improved.

According to another embodiment of the invention, the electrodes include both recording electrodes and stimulating electrodes.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
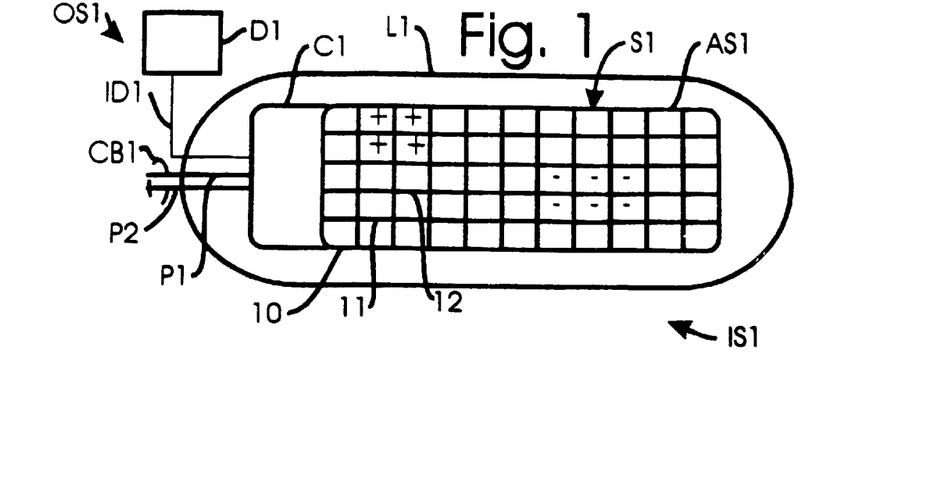
FIG. 1 is a top plan diagrammatic view of a preferred form of stimulation lead incorporating a stimulation assembly made in accordance with the present invention implanted within a patient and connected to a source of data.

Referring to FIG. 1, a preferred form of flat paddle lead L1 suitable for implantation into a patient basically comprises a stimulation assembly S1 that includes a controller C1 and an array of stimulating electrodes AS1. Lead L1 is implanted at a site IS1 within a patient adjacent tissue to be stimulated. Array AS1 includes fifty-five electrodes, such as flat electrodes 10–12, arranged in a rectangular grid and electrically insulated from each other. The top surface of array AS1 is exposed to patient tissue at the surface of lead L1. Controller C1 is connected to a conductor ID1 over which data is provided, from a data source D1, as well as a cable CB1 comprising power conductors P1 and P2 for conducting stimulating current to electrode array AS1. P1 and P2 are connected to a power source not shown. Controller C1 is coupled to each electrode in electrode array AS1 with separate conducting wires. Data source D1 is located at a site OS1 which could be located within the power source or at another location, usually subcutaneous. The data source may be a microprocessor including a memory for storing data that identifies electrodes to be activated and their polarities.

The FIG. 1 embodiment is especially good for red skeletal muscle, since stimulation on such a muscle can only activate the muscle fibers directly under the cathode. Action potentials do not spread from muscle fiber to fiber, as they do in smooth muscle or cardiac muscle. Hence, a broad array of cathodes is useful to recruit many fibers of a red muscle.

Figure 2:
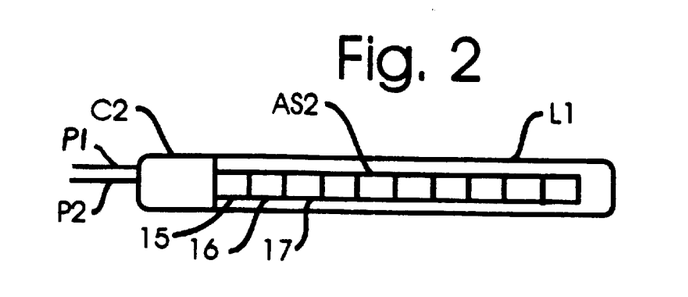
FIG. 2 is a side elevational view of the lead shown in FIG. 1.

Referring to FIG. 2, lead L1 also may optionally include another array of stimulating electrodes AS2, including electrodes such as 15–17, that is arranged on a side of lead L1. The surface of the electrodes in array AS2 is exposed at the side of lead L1 to electrically stimulate tissue of a patient at site IS1. Electrodes in array AS2 may be controlled by C1 and/or a separate controller C2 as shown.

Referring to FIG. 1, each electrode in array AS1 and AS2 is coupled to controller C1 and/or C2 via conductor wires. A signal is sent to controller C1 and/or C2 along conductor ID1 which identifies the electrodes to be activated. Controllers C1 and C2 act as switching gates coupling power lines P1 and P2 to the activated electrodes in array AS1 and AS2. Some activated electrodes may become cathodes (−) and other electrodes may become anodes (+). The plus signs and minus signs in FIG. 1 indicate electrodes which have been activated as anodes (+) and cathodes (−), respectively. Electrodes not chosen to be activated will be open circuit or will have a high impedance. The arrangement of anodes or cathodes on assembly S1 can be chosen by the patient or through investigation by clinicians to maximize the desired effects of stimulation, e.g., maximize pain relief, minimize spasticity, stop seizures, cause contraction of muscles, etc., and also to minimize undesirable side effects.

Still referring to FIG. 1, power conductors P1 and P2 carry the stimulation current necessary in order to stimulate the electrically excitable tissue adjacent lead L1. For monopolar stimulation, a single one of conductors P1 and P2 would suffice; but for bipolar stimulation, two power conductors (single channel), such as P1 and P2 are needed. For dual channel applications, three or four power conductors may be used. Fewer wires may suffice if the power signal is time division multiplexed.

Figure 9:
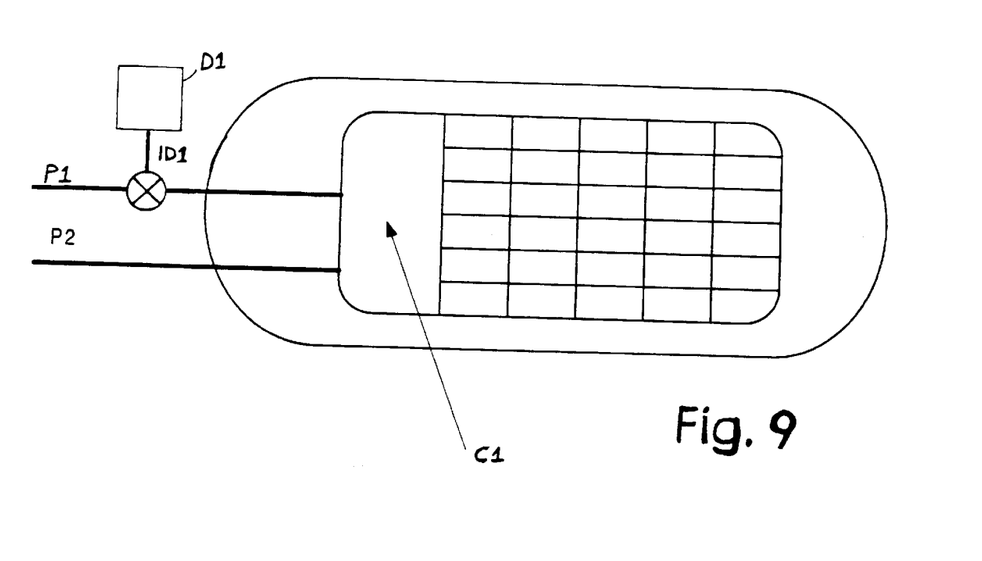
FIG. 9 is a top plan diagrammatic view of another form of the invention in which the data conductor and one of the power conductors are multiplexed into a single line.

FIG. 9 illustrates an embodiment of the present invention having two conductors leading to lead L1. Conductors P1 and ID1 of FIG. 1 are combined into a single conductor. The P1 and ID1 signals are modulated, thereby reducing the need for a third conductor. The modulation of the data signal of ID1 and the power signal of P1 or P2 may be accomplished by any number of modulation techniques including, but not limited to, Amplitude Modulation (AM), Frequency Shift Keying (FSK), Phase Shift Keying (PSK), pulse position timing and any combination thereof.

Referring back to FIG. 1, each of electrodes in arrays AS1 and AS2 is between 1–6 mm$^2$ in area, but other sizes also may be used. Typically, several neighboring electrodes are connected in parallel to have a combined surface area of 6–24 mm$^2$, but other sizes also may be beneficial. The electrodes in arrays AS1 and AS2 are electrically conductive, and usually are made from a metal like platinum or iridium. In FIG. 1, four electrodes have been programmed to be anodes (+) and six electrodes have been programmed to be cathodes (−).

The invention is useful in connection with electrically excitable tissue which includes both neural tissue and muscle tissue. Neural tissue includes peripheral nerves, the spinal cord surface, the deep spinal cord, deep brain tissue and brain surface tissue. Muscle tissue includes skeletal (red) muscle, smooth (white) muscle, and cardiac muscle.

Figure 3:
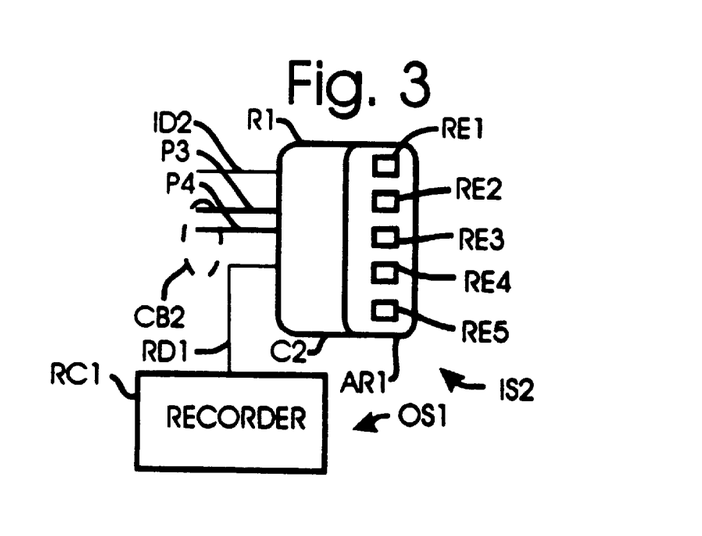
FIG. 3 is a top plan diagrammatic view of a preferred form of recording assembly made in accordance with the present invention.

FIG. 3 illustrates a preferred form of recording assembly R1 which includes a controller C2 and an array of recording electrodes RE1–RE5 electrically insulated from each other. Assembly R1 is implanted inside a patient at a site IS2. Controller C2 is provided with a conductor ID2 for transmitting data and a cable CB2 that includes power conductors P3 and P4, as well as an additional conductor RD1 used to transmit recorded and amplified tissue potentials received by one or more of conductors RE1–RE5. Conductor RD1 may be five separate conductors connected to electrodes RE1–RE5 or a single conductor on which potentials from electrodes RE1–RE5 are transmitted by time division multiplex techniques executed by controller C2. Alternatively, controller C2 might activate combinations of electrodes RE1–RE5 as stimulating electrodes to provide stimulation of tissue.

Recording assembly R1 can be used to record potentials in electrically excitable tissue. Controller C2 selects from among recording electrodes RE1–RE5, amplifies the signals received by the recording electrodes and sends the amplified signals over conductor RD1 to a recording instrument RC1. Controller C2 also could filter or otherwise process the signals. Instrument RC1 is located at another site, possibly OS1.

Referring to FIG. 3, under each recording electrode RE1–RE5 is an electrical circuit consisting of an operational amplifier and a gating circuit to turn on or turn off the recording electrode. A recording electrode may be chosen with optimal signal strength and discrimination of the potential of interest. Two or more electrodes may be connected together in parallel to lower impedance or may be used differentially to better shape the recorded potential and remove noise signals. Alternatively, controller C2 may control all signal conditioning functions and gating circuits, particularly if the dimensions of recording assembly R1 are small.

Conductor ID2 is used to carry data from a data source, such as D1, to controller C2. In response to the data, controller C2 activates the desired electrodes and adjusts the amplification. Cable CB2 is used to bring power to controller C2. Conductor RD1 exits from the recording site IS2 to bring the amplified recorded potentials to recorder RC1. The recording electrodes each typically have an impedance between 100,000 ohms and 1.5 megohms, but other impedances may be desirable.

Figure 4:
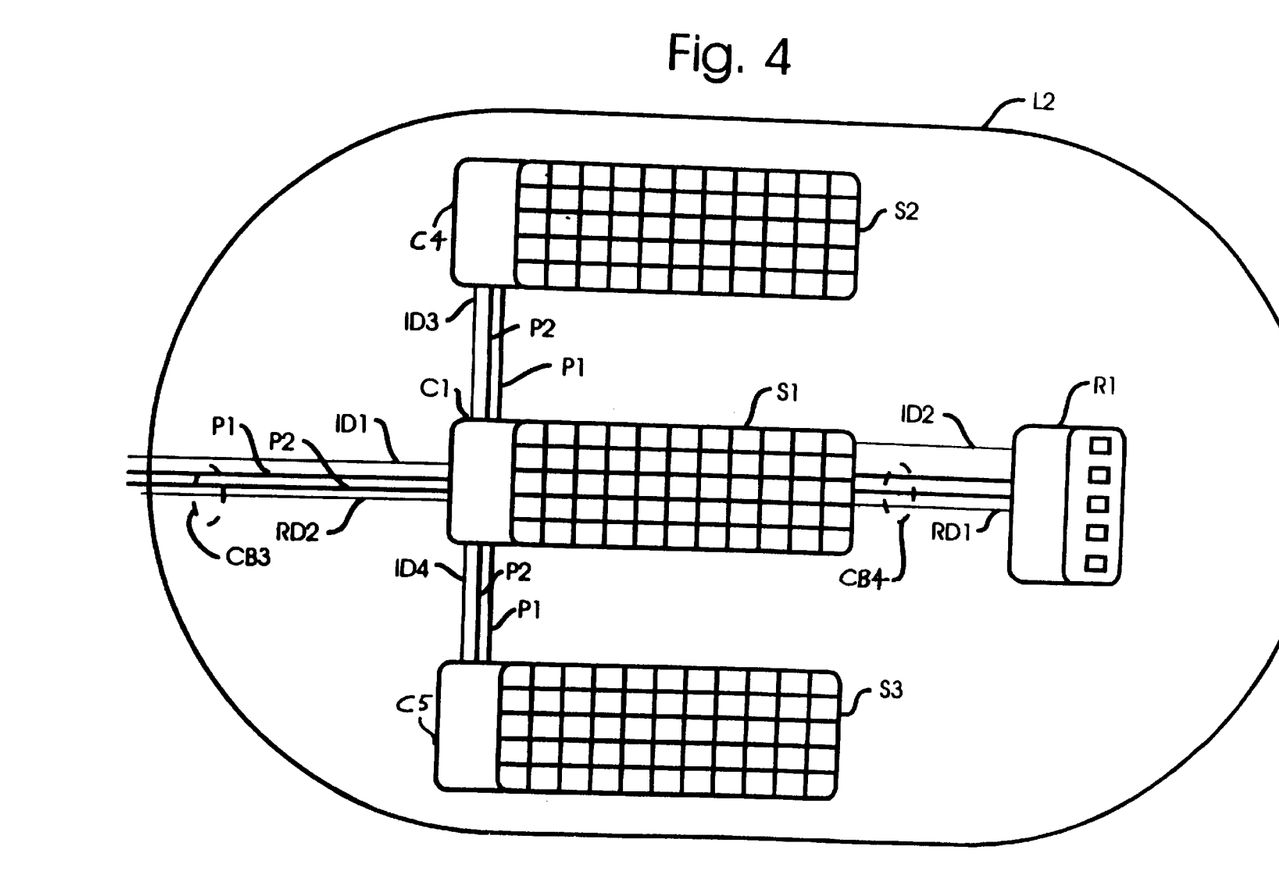
FIG. 4 is a top plan diagrammatic view of modified form of lead in which the stimulation assembly of FIG. 1 and the recording assembly of FIG. 3 are combined using multiple controllers.
Figure 5:
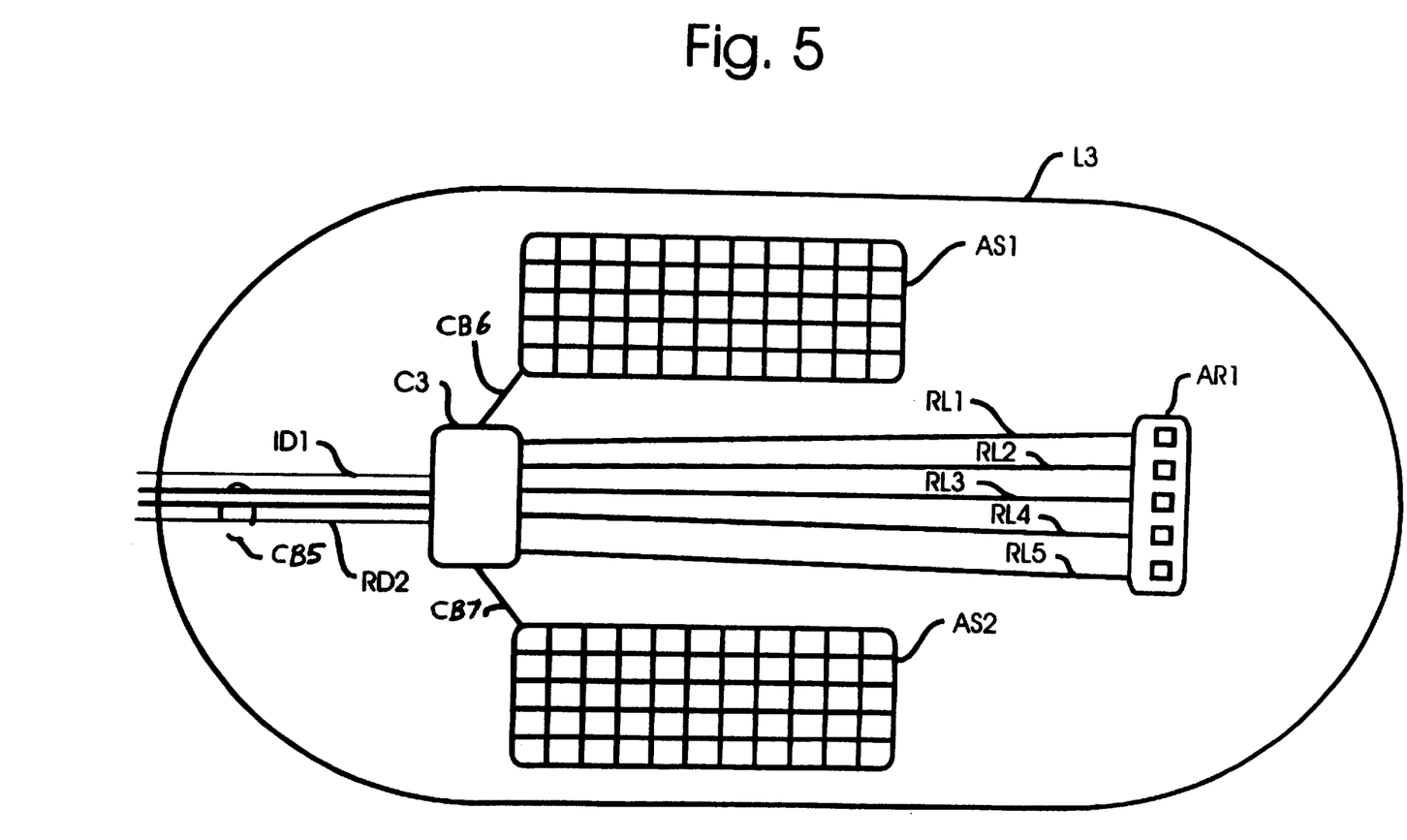
FIG. 5 is a top plan diagrammatic view of another form of the invention employing multiple arrays of stimulation electrodes and an array of recording electrodes that are controlled by a single controller.

FIGS. 4 and 5 show the flexibility of controllers and arrays of stimulation electrodes and optional recording electrodes made in accordance with the invention. Referring to FIG. 4, a lead L2 may comprise stimulating assembly S1 and optional recording assembly R1, as well as additional stimulating assemblies S2 and S3 that may be identical to assembly S1. Additional stimulating or recording assemblies may be added to S1 by the practitioner during implant. Conductor RD2 carries recorded potentials to a recorder, such as RC1 shown in FIG. 3. Conductor RD2 may be an extension of conductor RD1, or may contain additional data resulting from processing done in controller C1 of assembly S1. For the configuration shown in FIG. 4, controller C1 of assembly S1 may incorporate the functions of controllers C1 and C2 described in connection with FIGS. 1 and 3. Alternatively, controllers C4 and C5 may provide control to assemblies S2 and S3 respectively. Power is furnished to assemblies S2 and S3 by power conductors P1 and P2. A conductor ID3 communicates the data necessary to identify the stimulation electrodes within assembly S2 that need to be activated. A similar function is performed for assembly S3 by a data conductor ID4. Controller C1 processes the data on conductor ID1 in order to provide the appropriate data for assemblies S2 and S3 that is transmitted over conductors ID3 and ID4, respectively. With modulation of power signals on conductors P1 and P2, data conductors ID1, ID3 and ID4 may be unnecessary.

Referring to FIG. 5, a lead L3 carries a controller C3 that is connected to array AS1 and an identical array AS2, as well as array AR1. Each of the recording electrodes in array AR1 is connected to controller C3 by one of conductors RL1–RL5. Each of the stimulating electrodes on assembly AS1 is connected to controller C3 by a cable CB6, which contains individual conductors connected separately to each of the electrodes in assembly AS1. Similarly, each of the stimulating electrodes in assembly AS2 is connected to controller C3 through a cable CB7. Controller C3 receives information on conductor ID1 which identifies the electrodes of assemblies AS1 and AS2 which are to be activated, as well as the polarity of the electrodes. Controller C3 activates the electrodes in assemblies AS1 and AS2 in the same manner described in connection with controller C1 of FIG. 1.

The potentials transmitted by each of conductors RL1–RL5 are transmitted by controller C3 on a time division multiplex basis on output conductor RD2. RD2 may be connected to a recorder such as RC1 shown in FIG. 3.

Figure 6:
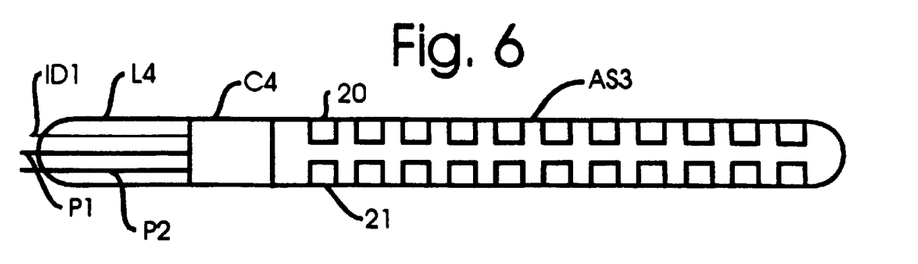
FIG. 6 is a side elevational diagrammatic view of another form of the invention employing multiple electrodes on a nearly cylindrical lead.
Figure 7:
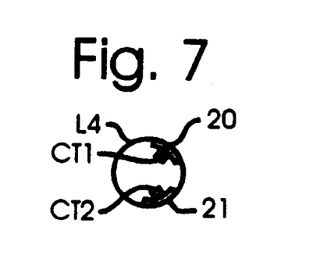
FIG. 7 is a diagrammatic end view of the lead shown in FIG. 6 and rotated slightly from the view shown in FIG. 6.
Figure 8:
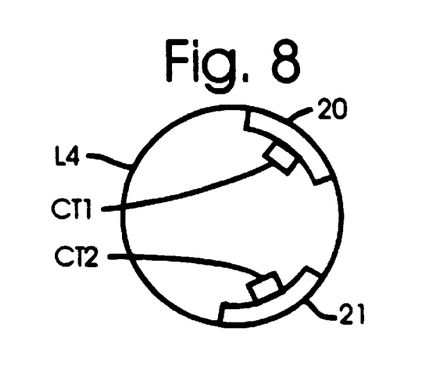
FIG. 8 is an enlarged view of FIG. 7.

FIG. 6 illustrates a generally cylindrical lead L4 carrying a controller C4 and an assembly of twenty-two stimulating electrodes AS3, including cylindrical electrodes 20 and 21 arranged as shown. Inside the body of lead L4 and mounted directly on electrodes 20 and 21 are corresponding electrical circuits CT1 and CT2 (FIGS. 7 and 8). For stimulating assembly AS3, circuits CT1 and CT2 are electrical switches or gates which activate specified electrodes in the assembly in accordance with the data received on conductor ID1. If there is only one electrode at each longitudinal position of the lead, it could be a ring electrode. If there is more than one electrode at each longitudinal position, the electrodes at each longitudinal position could occupy equal sectors of the cross-section of lead L4. Then, by use of controller C4, only those electrodes nearest the excitable tissue could be used for stimulating or recording. A complex lead may be assembled in the operating room by plugging any number of cylindrical extensions onto lead L4 (FIG. 6).

A recording assembly can be made in the same form as assembly AS3 shown in FIG. 6. In this case, the electrodes would perform the same recording function described in connection with FIG. 3. In such an embodiment, circuits CT1 and CT2 would be an amplifier and switchable gate that would transmit a tissue potential to controller C4.

Figure 10:
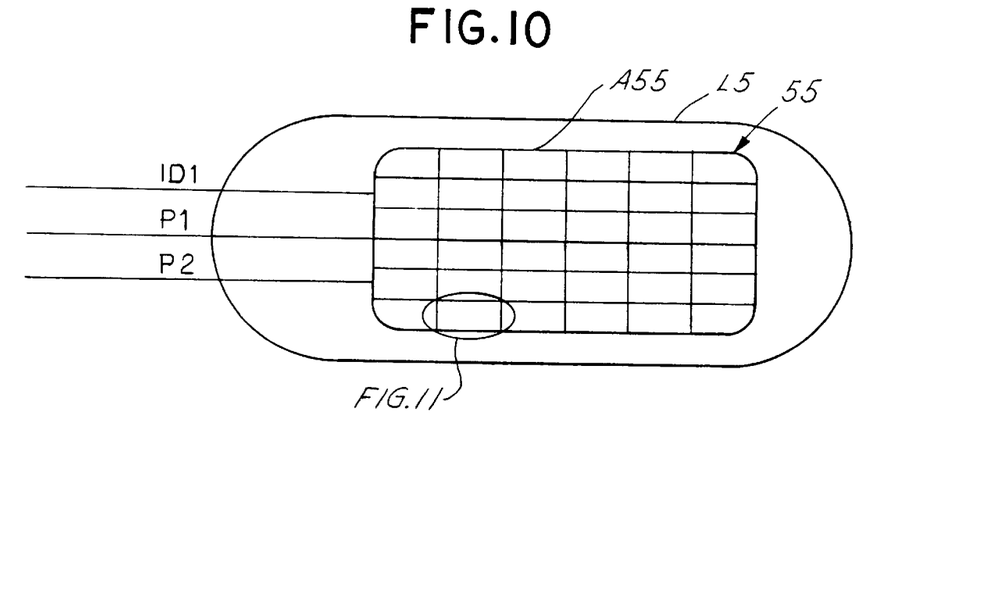
FIG. 10 is a top plan diagrammatic view of another form of the invention employing multiple controllers wherein each controller controls one or more of the stimulation electrodes in the array.
Figure 12:
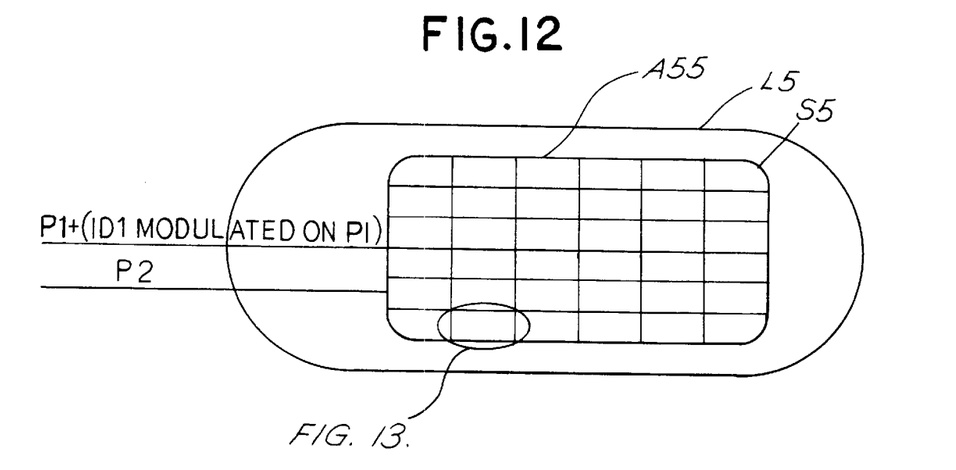
FIG. 12 is a top plan diagrammatic view of another form of the invention employing multiple controllers wherein each controller controls one or more of the stimulation electrodes in the array and a power conductor is modulated with a data conductor.

FIG. 10 is a top plan diagrammatic view of another embodiment of the invention employing multiple controllers wherein each controller controls one or more of the stimulation electrodes in the array. FIG. 10 illustrates a lead L5 having a stimulation assembly S5 that includes an array of controllers (not shown) and a corresponding array of stimulation electrodes AS5. Power conductors P1 and P2 and data signal ID1 connect to lead L1 similar to that of FIG. 1. Alternatively, as shown in FIG. 12, power conductor P1 may be modulated with data conductor ID1 using any number of modulation techniques thereby reducing the number of conductors to lead L5.

Figure 11:
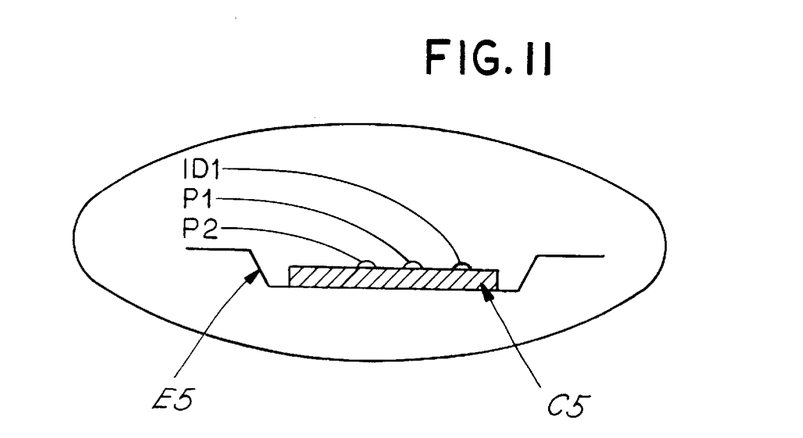
FIG. 11 is an exploded side elevational view of one of the stimulation electrodes of the lead shown in FIG. 10.
Figure 13:
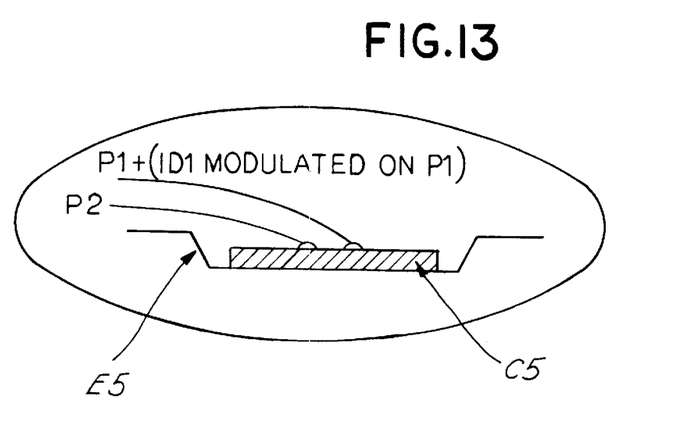
FIG. 13 is an exploded side elevational view of one of the stimulation electrodes of the lead shown in FIG. 12.

Referring to FIG. 10, each stimulation electrode with in the array AS5 has a corresponding controller which controls the operation of that electrode. Power signals P1 and P2 and data signal ID1 are provided to each of these individual controllers which in turn control the operation of the associated stimulation electrodes based on these signals. In such an embodiment, controller C1 (as shown in FIG. 1) would not be required. FIG. 11 is an exploded side elevational view of an individual controller C5 and the associated stimulation electrode E5 of lead L5. Power lines P1 and P2 and data line ID1 run to each controller in lead L5 including controller C5. Alternatively, as shown in FIG. 13, power conductor P1 may be modulated with data conductor ID1 using any number of modulation techniques thereby reducing the number of conductors to lead controller C5. FIG. 11 depicts a typical electrode/controller pair combination of lead L5. Controller C5 may be an integrated circuit (IC) and the conductors leading to controller C5 may be wirebonded to controller C5. Each electrode/controller pair has a unique address such that data conductor ID1 may designate which electrodes are to be activated based on the address information carried by the data conductor ID1. For each electrode designated for activation, the electrode is designated as an anode (+) or a cathode (−). As another embodiment, controller C5 may be positioned to control the operation of a number of electrodes. Controller C5 may also be used to control recording electrodes.

Each of assemblies AS1–AS3, AS5 and AR1 may be silicon wafers, and thus rigid. Controllers C1–C5 may be conventional microcontrollers capable of executing instructions stored in memory. Other parts of leads L1–L5 may be flexible and inert, or flexible and carry wires, such as assemblies AS1, AS2, and AR1 of FIG. 5. Flexible electrical circuits or ribbon cables also could be used to advantage.

Leads L1–L5 offer several advantages over known leads. One does not always know before implant what is the best strategy for lead placement and electrode polarity. Leads L1–L5 allow the choice to be made later, and additional reprogramming at later dates, to give degrees of freedom in electrode position. It is sometimes useful to have five or more electrodes in a line (especially transverse to the spinal cord axis), so that two or three can be chosen at preferred medial/lateral positions. The preferred embodiments enable changes in effective stimulation area after implant by programming only.

One key need for practitioners using spinal cord stimulation is to position one or more electrodes on the "physiological midline". This means that pulses will give balanced effects, and not be biased unduly on one or the other side (near one or the other dorsal root). When using the location of the vertebral canal for lead placement, only 27% of the time is the paresthesia balanced (Barolat, G., Zeme, S. and Ketcik, B., Multifactorial analysis of epidural spinal cord stimulation, Stereotact. Funct. Neurosurg., 56 (1991) 77–103. The preferred embodiments allow the "physiological midline" to be found by testing, and to be programmed accordingly.

Recording of electrical signals is quite difficult, and very dependent on distance from the active tissue, direction of action potentials in axons, and especially on the area/ impedance of the recording site (low impedance picks up potentials from larger distances, but signals are small). By picking the right locations of recording sites, and adding or subtracting neighboring site signals, the best signal can be obtained.

Being able to select and activate electrodes from a large number of possible sites provided by the preferred embodiments is valuable in case any site becomes unusable due to mechanical/electrical problems, scar tissue, etc. A near neighboring site might give almost as useful a result.

Currently the only way to select optimal electrode sites (beyond polarity choices) is by surgical positioning of the lead, which might be unreliable over time because positioning was done with the patient in one body position, and can change by migration of the lead. There have been proposals for leads that can have configuration changes, but these proposals do not offer the advantage of the preferred embodiments.

Advantageous uses for leads L1–L5 described in this specification include:

a. Over or in motor cortex or cerebellar cortex, where there are somatotopic maps of the body, and where fine control of the loci of excitation can help affect the movements or control of various body parts;

b. Over or in the sensory cortex, which also has a somatotopic map, so that paresthesia and/or motor effects can be adjusted to specific body parts;

c. In the thalamus, where there is a three-dimensional body map, and where there are lamina of cells that might best be activated (or partly activated) using many contacts and programming.

d. In deep tissue, where stimulation is advantageously achieved by cylindrical leads;

e. Transversely and over the cauda equina (nerves in the spinal canal descending from the tip of the cord) to enable great selectivity of stimulation;

f. In the cochlea, where there is insufficient space for many wires, but many channels are needed and where fine-tuning which sites along the cochlea get stimulated might lead to much better hearing;

g. Over branches of motor nerves or large nerves, to activate distinct fascicles; and h. In the retina, where if a patient has no light going to the back of the eye, the preferred embodiment could stimulate in neural patterns as if light were going there in focus and being perceived.

The controller chips disclosed in this specification preferably are rigid, made on silicone, with a hermetically sealed cover. However, they may be quite small. All other parts of leads L1–L5 may be flexible.

Another advantage of leads L1–L5 is that a number of recording sites could be programmed in parallel to constitute a stimulation site which generally requires a low impedance and larger surface area. Several stimulation sites may be programmed together to reduce the impedance.

Those skilled in the art recognize that the preferred embodiments may be altered and modified without departing from the true spirit and scope of the invention as defined in the appended claims. For example, the electrodes may be planar and of any shape (e.g., round, oval, and rectangular). The electrodes also may have three dimensional outer surface (e.g., cylindrical, spherical, semispherical or conical).

We claim:

1. Apparatus for interacting with electrically excitable tissue of a patient comprising:

a group of implantable electrodes adapted to interact with said tissue, said group of electrodes being arranged on at least one implantable lead to form at least one array wherein each electrode is adjacent at least one other of said electrodes;

a main cable having at least one power conductor adapted to extend to a site adjacent said tissue wherein the number of said power conductors is fewer than the number of said electrodes;

a source of data;

a data conductor adapted to extend to said site adjacent said tissue from said source of data; and implantable controller means in communication with said source of data and responsive to said data for gating to said main cable at least one pair of nonadjacent electrodes within said group to establish an anode and cathode relationship between said pair of nonadjacent electrodes.

2. Apparatus, as claimed in claim 1, wherein said group of electrodes comprises stimulating electrodes for stimulating said tissue.

3. Apparatus, as claimed in claim 1, wherein said group of electrodes comprises recording electrodes for conducting potentials found in said tissue.

4. Apparatus, as claimed in claim 3, wherein said recording electrodes are connected in parallel to form at least one stimulating electrode.

5. Apparatus, as claimed in claim 1, wherein said source of data comprises adaptions at a site remote from said site adjacent to said tissue and wherein said data conductor comprises adaptions for extending from said remote site to said site adjacent said tissue.

6. Apparatus, as claimed in claim 1, wherein said controller means comprises a group of switchable gates interconnecting said main cable with said at least one selected electrode.

7. Apparatus, as claimed in claim 1, wherein said controller means comprises a group of at least one integrated circuit wherein each of said integrated circuit within said group is capable of interconnecting said main cable with said at least one electrode.

8. Apparatus, as claimed in claim 1, wherein said group of implantable electrodes comprises a first plurality of stimulating electrodes for stimulating said tissue and a second plurality of recording electrodes for conducting potentials in said tissue, wherein said main cable comprises a power conductor and a recording conductor, wherein said source of data comprises a first source identifying at least one of said stimulating electrodes and at least one of said recording electrodes, and wherein said controller means comprises means for gating said selected at least one stimulating electrode to said power conductor and for gating said selected at least one recording electrode to said recording conductor.

9. Apparatus, as claimed in claim 8, wherein said controller means comprises multiplex means for transmitting signals between said at least one recording electrode and said recording conductor by time division multiplexing.

10. Apparatus, as claimed in claim 8, wherein said first plurality of said stimulating electrodes comprises a first array of stimulating electrodes and a second array of stimulating electrodes spaced from said first array, said first array being connected to said controller means by a first cable and said second array being connected to said controller means by a second cable.

11. Apparatus, as claimed in claim 8, and further comprising a third plurality of stimulating electrodes spaced from said first plurality of stimulating electrodes and a second controller means displaced from said controller means for gating said third plurality of stimulating electrodes, said controller means and said second controller means being connected by a second main cable.

12. Apparatus, as claimed in claim 1, wherein said implantable controller means is further adapted for gating to said main cable a first plurality of adjacent electrodes to together provide a first combined electrode adapted to cooperate in said anode and cathode relationship with at least one electrode within said group.

13. Apparatus, as claimed in claim 12, wherein said implantable controller means is further adapted for gating to said main cable a second plurality of adjacent electrodes to together provide a second combined electrode adapted to cooperate in said anode and cathode relationship with said first combined electrode.

14. Apparatus, as claimed in claim 1, wherein said group of implantable electrodes comprises a first plurality of stimulating electrodes, wherein said first plurality of said stimulating electrodes comprises a first array of stimulating electrodes and a second array of stimulating electrodes spaced from said first array, said first array being connected to said controller means by a first cable and said second array being connected to said controller means by a second cable.

15. Apparatus for interacting with electrically excitable tissue of a patient comprising:
   a group of implantable electrodes adapted to interact with said tissue, said group of electrodes being arranged on at least one implantable lead to form at least one array wherein each electrode is adjacent at least one other of said electrodes;
   a main cable adapted to extend to a site adjacent said tissue and having at least one power conductor, a data conductor and a multiplexor for coupling at least one of said power conductors and said data conductor, wherein the number of said power conductors is fewer than the number of said electrodes;
   a source of data; and
   implantable controller means in communication with said source of data and responsive to said data for gating to said main cable at least one pair of nonadjacent electrodes within said group to establish an anode and cathode relationship between said pair of nonadjacent electrodes.

16. Apparatus for interacting with electrically excitable tissue of a patient, comprising:
   a group of implantable electrodes adapted to interact with said tissue, said group of implantable electrodes comprising a first plurality of stimulating electrodes for stimulating said tissue and a second plurality of recording electrodes for conducting potentials in said tissue, said first plurality of stimulating electrodes comprising a first array of stimulating electrodes and a second array of stimulating electrodes spaced from said first array;
   a main cable adapted to extend to a site adjacent said tissue, said main cable comprising a power conductor and a recording conductor;
   a source of data comprising a first source identifying at least one of said stimulating electrodes and at least one of said recording electrodes;
   a data conductor adapted to extend to said site adjacent said tissue from said source of data; and
   implantable controller means in communication with said source of data and responsive to said data for gating said selected at least one stimulating electrode to said power conductor and for gating said selected at least one recording electrode to said recording conductor, said controller means being connected to said first array of stimulating electrodes by a first cable and to said second array of stimulating electrodes by a second cable, whereby electrical signals can be transmitted between said first site and said at least one selected electrode with a minimum number of conductors.

17. Apparatus for interacting with electrically excitable tissue of a patient, comprising:
   a group of implantable electrodes adapted to interact with said tissue, said group of implantable electrodes comprising a first plurality of stimulating electrodes for stimulating said tissue, a second plurality of recording electrodes for conducting potentials in said tissue, and a third plurality of stimulating electrodes spaced from said first plurality of stimulating electrodes;
   a main cable adapted to extend to a site adjacent said tissue, said main cable comprising a power conductor and a recording conductor;
   a source of data comprising a first source identifying at least one of said stimulating electrodes and at least one of said recording electrodes;
   a data conductor adapted to extend to said site adjacent said tissue from said source of data;
   implantable controller means in communication with said source of data and responsive to said data for gating said at least one of said electrodes to said main cable, said controller means comprising means for gating said selected at least one stimulating electrode to said power conductor and for gating said selected at least one recording electrode to said recording conductor;
   a second controller means displaced from said controller means for gating said third plurality of stimulating electrodes; and
   a second main cable connecting said controller means and said second controller means, whereby electrical signals can be transmitted between said first site and said at least one selected electrode with a minimum number of conductors.

18. A method of interacting with electrically excitable tissue of a patient by means of a main cable comprising the steps of:
   implanting a group of electrodes adapted to interact with said tissue, said group of electrodes being arranged to form at least one array wherein at least one electrode is adjacent at least one other of said electrodes;
   extending a main cable having at least one power conductor from a site adjacent said tissue to a site remote from said site adjacent said tissue wherein the number of said power conductors is fewer than the number of said electrodes;
   selecting at least one of said electrodes within said group; and
   gating said selected electrode to said main cable to establish an anode and cathode relationship between at least one pair of nonadjacent electrodes, whereby electrical signals can be transmitted to or from said tissue with a minimum number of conductors.

19. A method, as claimed in claim 18, wherein said group of electrodes comprises stimulating electrodes for stimulating said tissue.

20. A method, as claimed in claim 18, wherein said group of electrodes comprises recording electrodes for conducting potentials found in said tissue.

21. A method, as claimed in claim 18, wherein said group of electrodes comprises a first plurality of stimulating electrodes for stimulating said tissue and a second plurality of recording electrodes for conducting potentials in said tissue, wherein said main cable comprises a power conductor and a recording conductor, wherein said step of selecting comprises the step of selecting at least one of said stimulating electrodes and at least one of said recording electrodes, and wherein said step of gating comprises the step of gating said selected at least one stimulating electrode to said power conductor and the step of gating said selected at least one recording electrode to said recording conductor.

22. A method, as claimed in claim 21, wherein said step of gating comprises the step of transmitting signals between said at least one recording electrode and said recording conductor by time division multiplexing.

23. A method, as claimed in claim 18, wherein a first plurality of adjacent electrodes are gated to said main cable to together provide a first combined electrode adapted to cooperate in said anode and cathode relationship with at least one electrode within said group that is non-adjacent said first combined electrode.

24. A method, as claimed in claim 23, wherein a second plurality of adjacent electrodes that are each non-adjacent said first combined electrode are gated to said main cable to together provide a second combined electrode adapted to cooperate in said anode and cathode relationship with said first combined electrode.

25. A method of interacting with electrically excitable tissue of a patient by means of a main cable, comprising the steps of:

implanting a group of electrodes adapted to interact with said tissue;

extending a main cable having at least one power conductor from a site adjacent said tissue to a site remote from said site adjacent said tissue wherein the number of said power conductors is fewer than the number of said electrodes;

selecting at least two of said electrodes within said group; and gating said selected electrodes to said main cable, whereby electrical signals can be transmitted to or from said tissue with a minimum number of power conductors.

26. A method, as claimed in claim 25, wherein said group of electrodes comprises stimulating electrodes for stimulating said tissue.

27. A method, as claimed in claim 25, wherein said group of electrodes comprises recording electrodes for conducting potentials found in said tissue.

28. A method, as claimed in claim 25, wherein said group of electrodes comprises a first plurality of stimulating electrodes for stimulating said tissue and a second plurality of recording electrodes for conducting potentials in said tissue, wherein said main cable comprises a power conductor and a recording conductor, wherein said step of selecting comprises the step of selecting at least one of said stimulating electrodes and at least one of said recording electrodes, and wherein said step of gating comprises the step of gating said selected at least one stimulating electrode to said power conductor and the step of gating said selected at least one recording electrode to said recording conductor.

29. A method, as claimed in claim 28, wherein said step of gating comprises the step of transmitting signals between said at least one recording electrode and said recording conductor by time division multiplexing.

30. A method, as claimed in claim 25, wherein a first plurality of adjacent electrodes are gated to said main cable to together provide a first combined electrode adapted to cooperate in an anode and cathode relationship with at least one electrode within said group that is non-adjacent said first combined electrode.

31. A method, as claimed in claim 30, wherein a second plurality of adjacent electrodes that are each non-adjacent said first combined electrode are gated to said main cable to together provide a second combined electrode adapted to cooperate in said anode and cathode relationship with said first combined electrode.

* * * * *

UNITED STATES PATENT AND TRADEMARK OFFICE
CERTIFICATE OF CORRECTION

PATENT NO. : 6,038,480
DATED : MARCH 14, 2000
INVENTOR(S) : GARY W. KING AND GREGORY A. HRDLICKA

It is certified that error appears in the above-identified patent and that said Letters Patent are hereby corrected as shown below:

COLUMN 12, LINE 31, "...cooperate in an anode and..." should be "...cooperate in said anode and..."

Signed and Sealed this

Seventeenth Day of April, 2001

Attest:

NICHOLAS P. GODICI

Attesting Officer       Acting Director of the United States Patent and Trademark Office